(12) United States Patent
Durant et al.

(10) Patent No.: US 9,408,668 B2
(45) Date of Patent: Aug. 9, 2016

(54) SURGICAL INSTRUMENT WITH CONTROL FOR DETECTED FAULT CONDITION

(75) Inventors: Kevin Durant, Alameda, CA (US); Gabriel F. Brisson, Albany, CA (US); Scott E. Manzo, Shelton, CT (US); William A. Burbank, Sandy Hook, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 453 days.

(21) Appl. No.: 13/483,444

(22) Filed: May 30, 2012

(65) Prior Publication Data
US 2012/0310221 A1    Dec. 6, 2012

Related U.S. Application Data

(60) Provisional application No. 61/491,671, filed on May 31, 2011, provisional application No. 61/491,698, filed on May 31, 2011.

(51) Int. Cl.
*A61B 17/00* (2006.01)
*G06F 19/00* (2011.01)
*B25J 9/18* (2006.01)
*A61B 19/00* (2006.01)

(52) U.S. Cl.
CPC ............. *A61B 19/2203* (2013.01); *A61B 19/22* (2013.01); *A61B 2017/00017* (2013.01); *A61B 2017/00119* (2013.01); *A61B 2019/2242* (2013.01)

(58) Field of Classification Search
CPC ............... A61B 19/22; A61B 19/2203; A61B 2019/2242

USPC ............................. 606/1; 700/245; 318/568.11
See application file for complete search history.

(56) References Cited

U.S. PATENT DOCUMENTS

| | | | |
|---|---|---|---|
| 6,565,554 | B1 | 5/2003 | Niemeyer |
| 8,758,342 | B2 | 6/2014 | Bales et al. |
| 2007/0175956 | A1 | 8/2007 | Swayze et al. |

(Continued)

FOREIGN PATENT DOCUMENTS

| | | |
|---|---|---|
| CN | 101133972 A | 3/2008 |
| CN | 101471596 A | 7/2009 |

(Continued)

OTHER PUBLICATIONS

International Search Report and Written Opinion for Application No. PCT/US2012/040016, mailed on Oct. 4, 2012, 10 pages.

(Continued)

*Primary Examiner* — Lynsey Crandall
*Assistant Examiner* — Sebastian X Lukjan

(57) ABSTRACT

A medical device may include a surgical instrument and a controller. The surgical instrument may include an end effector component configured to move from a first position to a second position and the controller may be operatively coupled to control movement of the end effector component. The controller may further be configured to command the end effector component to move from the first position toward the second position, and automatically oscillate the end effector component if the controller has not received a signal indicating the end effector has reached a preset location within a predetermined time period after the controller commands the end effector component to move from the first position toward the second position.

16 Claims, 14 Drawing Sheets

(56) References Cited

U.S. PATENT DOCUMENTS

| | | |
|---|---|---|
| 2007/0239120 A1 | 10/2007 | Brock et al. |
| 2009/0138006 A1 | 5/2009 | Bales et al. |
| 2009/0167214 A1 | 7/2009 | Masuo et al. |
| 2009/0326557 A1 | 12/2009 | Niemeyer |
| 2011/0028894 A1* | 2/2011 | Foley et al. ............ 604/95.01 |
| 2011/0071676 A1* | 3/2011 | Sanders et al. ............ 700/250 |
| 2012/0215220 A1 | 8/2012 | Manzo et al. |
| 2012/0310254 A1 | 12/2012 | Manzo et al. |

FOREIGN PATENT DOCUMENTS

| | | |
|---|---|---|
| EP | 1813207 A1 | 8/2007 |
| EP | 1815950 A1 | 8/2007 |

OTHER PUBLICATIONS

International Search Report and Written Opinion for Application No. PCT/US2012/040029, mailed on Oct. 4, 2012, 10 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Office Action mailed Jul. 1, 2015 for Chinese Application No. 201280026691.1 filed May 30, 2012.

* cited by examiner

SURGICAL INSTRUMENT WITH CONTROL FOR DETECTED FAULT CONDITION

CROSS-REFERENCE TO RELATED APPLICATION

This application claims priority to U.S. Provisional Patent Application No. 61/491,671 filed on May 31, 2011, and to U.S. Provisional Patent Application No. 61/491,698, filed on May 31, 2011, each of which is incorporated by reference in its entirety herein.

This application is related to co-pending U.S. patent application Ser. No. 13/483,410, entitled "SURGICAL INSTRUMENT WITH MOTOR," filed on a date even herewith, having a common assignee, and claiming priority to U.S. Provisional Application No. 61/491,698, filed May 31, 2011.

TECHNICAL FIELD

Aspects of the present disclosure relate to surgical instruments that are minimally invasive and control techniques for such instruments. More particularly, aspects of the present disclosure relate to detecting a position of an end effector component of a surgical instrument to control the instrument. For example, aspects of the present disclosure include detecting a fault condition of the surgical instrument, based on its detected position, and performing control operations to rectify the fault condition.

INTRODUCTION

Minimally invasive surgical techniques generally attempt to perform surgical procedures while minimizing damage to healthy tissue. Some minimally invasive surgical procedures are performed remotely through the use of robotically-controlled surgical instruments. In robotically-controlled surgical systems, surgeons manipulate input devices at a surgeon side console, and a patient side console that interfaces with a robotically-controlled surgical instrument is able to operate on a patient based on the surgeon's inputs at the surgeon side console.

Minimally invasive surgical instruments, whether manually or robotically actuated may be used in a variety of operations and have various configurations. Many such instruments include a surgical end effector mounted at a distal end of a long shaft that is configured to be inserted (e.g., laporoscopically or thoracoscopically) through an opening (e.g., body wall incision, natural orifice) to reach a remote surgical site. In some instruments, an articulating wrist mechanism is mounted to the distal end of the instrument's shaft to support the end effector and alter an orientation with reference to the shaft's longitudinal axis.

End effectors may be configured to perform various functions so as to be able to perform any of a variety of surgical procedures. Examples include, but are not limited to, cauterizing, ablating, suturing, cutting, stapling, etc., and combinations thereof. Accordingly, end effectors can include a variety of components and/or combinations of components to perform these surgical procedures.

Actuation of the end effector to perform a surgical procedure is generally accomplished through the use of input at a proximal end of the surgical instrument, whether manually or robotically, and various gears, levers, pulleys, etc. are used to transmit the input to actuate the end effector. In the case of robotically-controlled surgical instruments, a transmission mechanism at the proximal end of the instrument interfaces with various servo actuators provided on a robotic arm of a patient side console (also referred to as a patient side cart). The servo actuators receive signals through a master controller and provide input, e.g., to input drives (e.g., rotating shafts) at the transmission mechanism, which the various gears, levers, rack and pinions, pulleys, etc. ultimately transmit to actuate the end effector.

In light of the remote nature of the operation of such end effectors, it may be difficult in some cases for a surgeon to know the position of a component of the end effector during actuation to perform a surgical procedure. For example, in some cases, other portions of the surgical instrument, including the end effector itself, and/or parts of the patient's body can hide from view a component during the actuation procedure. Also, if an end effector component encounters a fault condition when attempting to perform a surgical procedure for which it has been actuated, it may be difficult to correct the fault condition due to the limited space in which the instrument operates and consequent limited access to the instrument, as well as the remote position of the end effector from the surgeon.

It may therefore be desirable to provide a technique to detect the position of an end effector during actuation. For example, it may be desirable to detect the position of an end effector to determine whether or not the end effector has successfully performed the desired surgical procedure for which it was actuated. It also may be desirable to provide automatic control of a surgical instrument to perform various actions if a surgical procedure is not completed or if the end effector does not reach an anticipated position when performing a surgical procedure.

SUMMARY

The present teachings may solve one or more of the above-mentioned problems and/or may demonstrate one or more of the above-mentioned desirable features. Other features and/or advantages may become apparent from the description that follows.

In accordance with various exemplary embodiments of the present teachings, the present teachings contemplate a method of controlling a surgical instrument comprising an end effector. The method includes detecting a first signal indicating that an end effector component of a surgical instrument is positioned between a first position and a second position, and automatically controlling operation of the end effector component after a second signal is not received within a predetermined time period after detecting the first signal. The second signal indicates that the end effector component is in one of the first position or the second position.

In accordance with at least one exemplary embodiment, the present teachings contemplate a system for detecting a fault condition of a surgical instrument. The system includes a surgical instrument and a controller. The surgical instrument includes an end effector component configured to move between a first position and a second position. The controller is in signal communication with the surgical instrument and is configured to detect a first signal indicating that the end effector component is positioned between the first position and the second position and to detect a second signal indicating that the end effector component is in one of the first position or the second position. The controller is further configured to transmit a control signal to control the end effector component after the second signal is not received within a predetermined time period after the controller detects the first signal.

Additional objects and advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the invention, as claimed; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

This description and the accompanying drawings that illustrate exemplary embodiments should not be taken as limiting, with the claims defining the scope of the present disclosure. Various mechanical, compositional, structural, electrical, and operational changes may be made without departing from the scope of this description and the invention as claimed, including equivalents. In some instances, well-known structures, and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Figure 1:
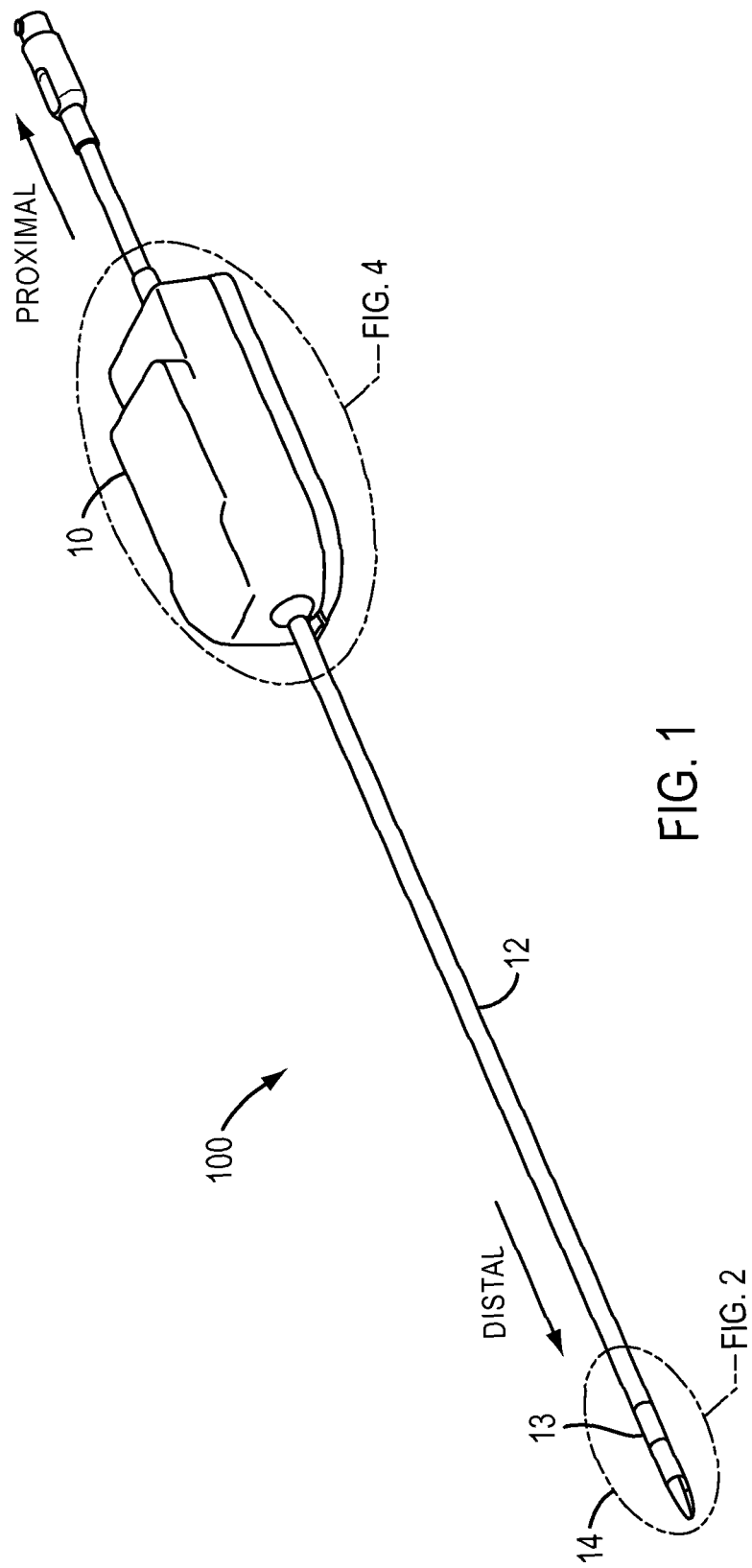
FIG. 1 is a perspective view of a minimally invasive surgical instrument in accordance with an exemplary embodiment of the present disclosure.
Figure 2:
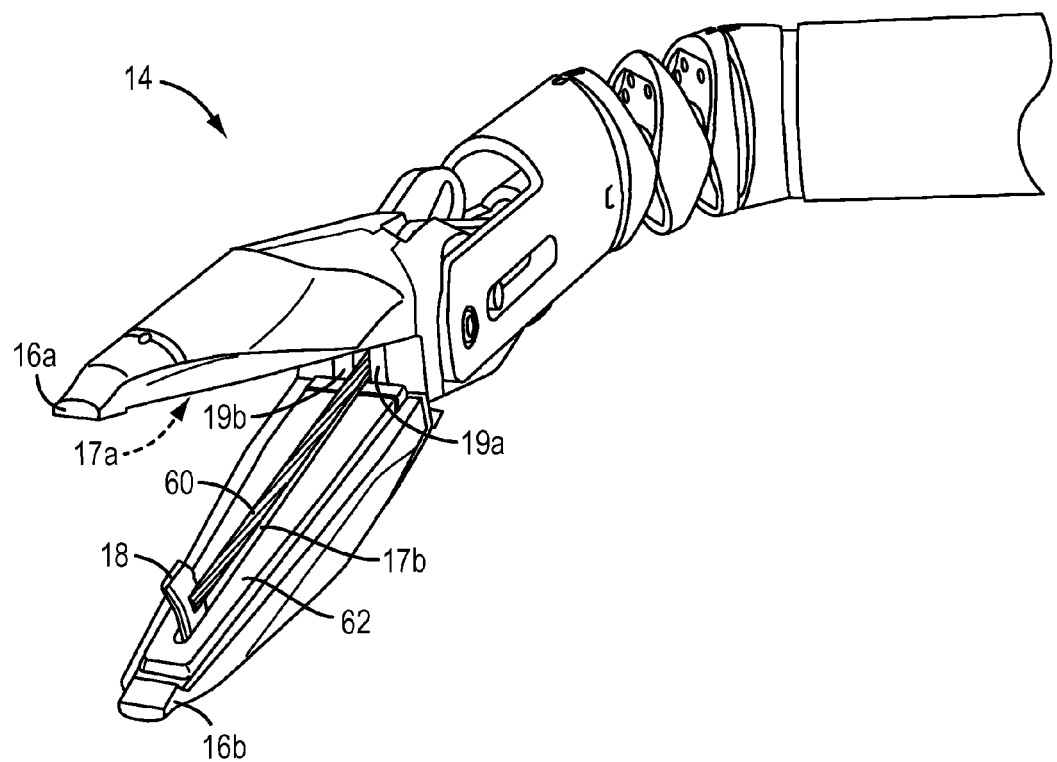
FIG. 2 is a perspective view of an end effector corresponding to a portion of the surgical instrument of FIG. 1 in accordance with an exemplary embodiment.

With reference now to FIG. 1, a minimally invasive surgical instrument 100 in accordance with an exemplary embodiment of the present disclosure is depicted. FIG. 1 is a perspective view of the minimally invasive surgical instrument 100, and FIGS. 2 and 4 show detailed views of exemplary, non-limiting embodiments of the corresponding portions denoted in FIG. 1 that the surgical instrument 100 can include. The directions "proximal" and "distal" are used herein to define the directions as shown in FIG. 1, with distal generally being in a direction further along a kinematic arm or closest to the surgical work site in the intended operational use of the instrument 100, for example, in use for performing surgical procedures. As shown in FIG. 1, the instrument 100 generally includes a force/torque drive transmission mechanism 10 at its proximal end, an instrument shaft 12 mounted to the transmission mechanism 10, and an end effector 14 disposed at the distal end of the shaft 12. In the exemplary embodiment shown in FIG. 1, the surgical instrument 100 also includes an optional articulating wrist mechanism 13 mounted at the distal end of the shaft 12 to support the end effector 14 and change its orientation with reference to the shaft's 12 longitudinal axis.

Figure 12A:
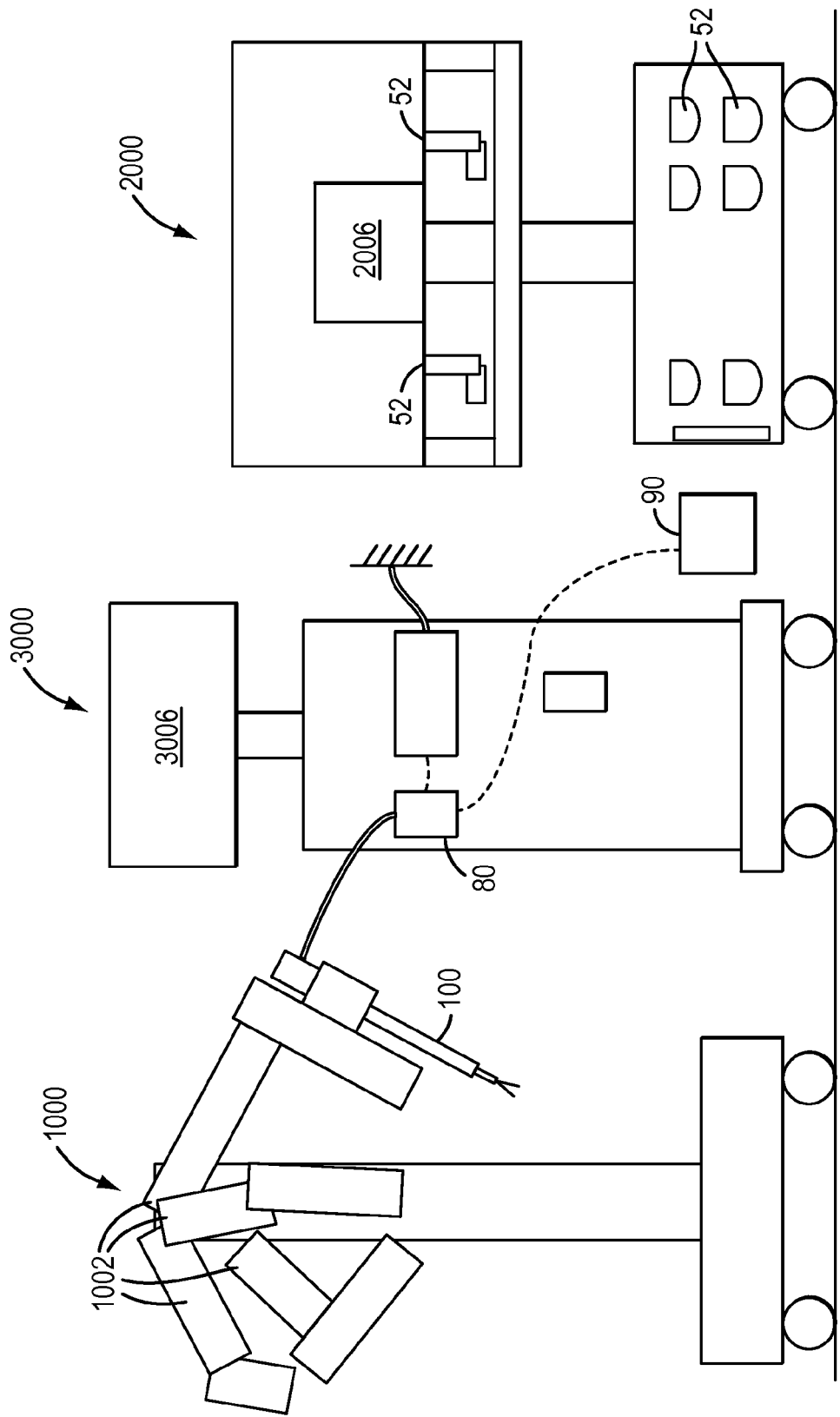
FIG. 12A is a schematic view of an exemplary robotic surgical system configured to operate a robotically-controlled surgical instrument in accordance with an exemplary embodiment.
Figure 12B:
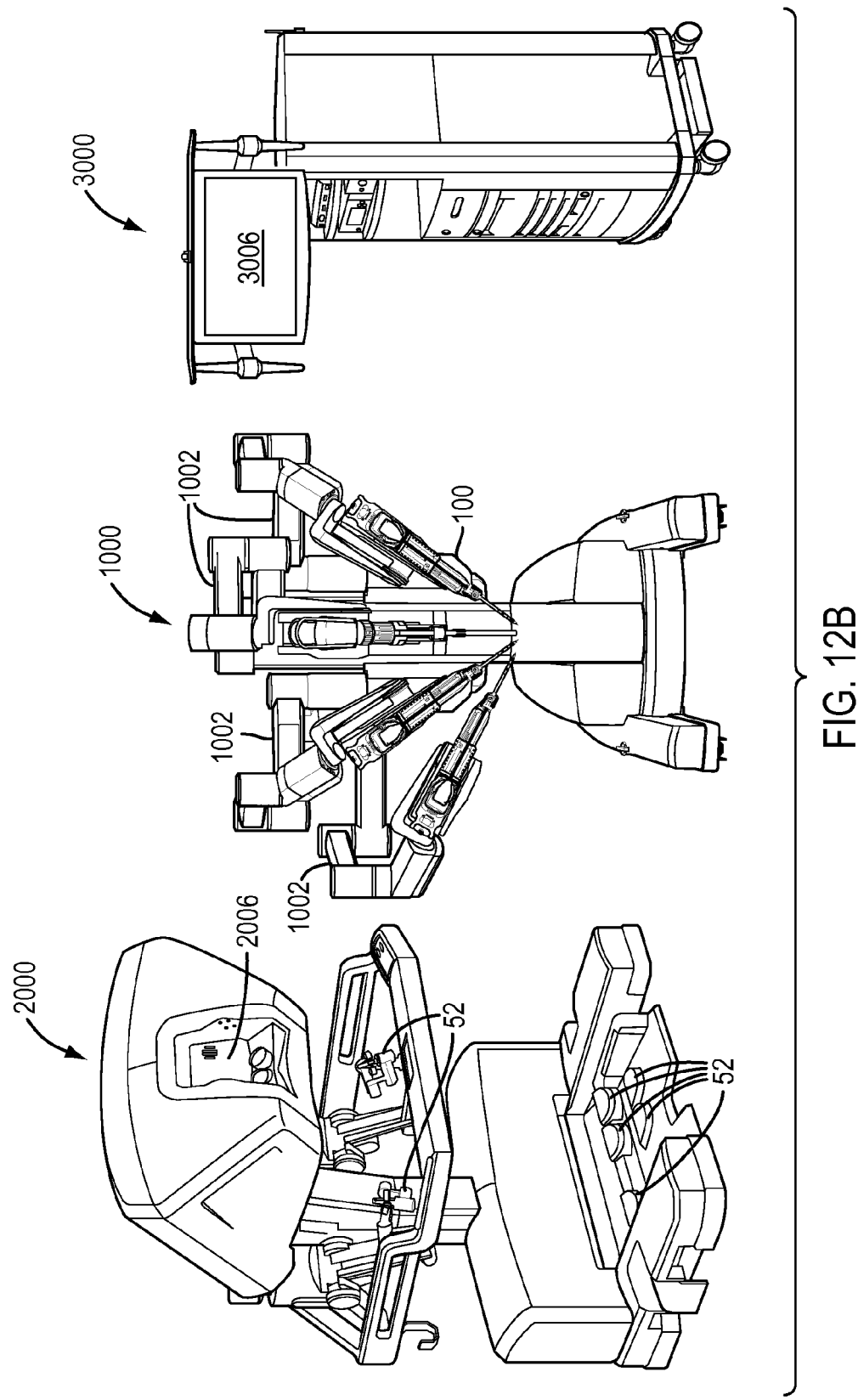
FIG. 12B is an diagrammatic view of the system of FIG. 12A.

In an exemplary embodiment, the instrument 100 is configured to be mounted on and used with a minimally invasive surgical robotic system, which in an exemplary embodiment includes a patient side console 1000, a surgeon side console 2000, and an electronics/control console 3000, as illustrated in the schematic view of FIG. 12A and in an diagrammatic view of FIG. 12B (it is noted that the system components in FIGS. 12A and 12B are not shown in any particular positioning and can be arranged as desired, with the patient side console being disposed relative to the patient so as to effect surgery on the patient). A non-limiting, exemplary embodiment of a surgical robotic system with which the instrument 100 can be utilized is a da Vinci® Si (model no. IS3000) commercialized by Intuitive Surgical, Inc. of Sunnyvale, Calif.

The robotic surgical system is used to perform minimally invasive robotic surgery by interfacing with and controlling a variety of surgical instruments, as those of ordinary skill in the art are generally familiar. The patient side console 1000 includes various arms for holding and manipulating various tools. As shown in FIGS. 12A and 12B, one arm is configured to interface with and control a robotically-controlled surgical instrument 100, including an end effector 14. In general, the surgeon side console 2000 receives inputs from a surgeon by various input devices, including but not limited to, gripping mechanisms and foot pedals 52, etc. and serves as a master controller by which the patient side console 1000 acts as a slave to implement the desired motions of the surgical instrument(s) (e.g., instrument 100) interfaced therewith, and accordingly perform the desired surgical procedure. The surgeon side console 2000 also can include a viewer or display 2006 that allows the surgeon to view a three-dimensional image of the surgical site. The patient side console 1000 can include a plurality of jointed arms 1002 configured to hold various tools, including, but not limited to, for example, a surgical instrument with an end effector (e.g., surgical instrument 100), and an endoscope (not shown). Based on the commands input at the surgeon side console 2000, the patient side console 1000 can interface with a transmission mechanism of the surgical instrument to position and actuate the instrument to perform a desired medical procedure. The electronics/control console 3000 receives and transmits various control signals to and from the patient side console 1000 and the surgeon side console 2000, and can transmit light and process images (e.g., from an endoscope at the patient side console 1000) for display, such as, e.g., display 2006 at the surgeon side console 2000 and/or on a display 3006 associated with the electronics/control console 3000. Those having ordinary skill in the art are generally familiar with such robotically controlled surgical systems.

In an exemplary embodiment, the electronics/control console 3000 may have all control functions integrated in one or more controllers in the electronics/control console 3000, or additional controllers may be provided as separate units and supported (e.g., in shelves) on the electronics/control console 3000 for convenience. The latter may be useful, for example, when retrofitting existing electronics/control consoles to control surgical instruments requiring additional functionality. Likewise, although in various exemplary embodiments, one or more input mechanisms may be integrated into the surgeon side console 2000, various other input mechanisms may be added separately and provided so as to be accessible to the surgeon during use of the system, but not necessarily integrated into the surgeon side console 2000.

Accordingly, as used herein, the term "electronics/control console" and variations thereof should be understood to include a console wherein one or more controllers (e.g., processors, such as processor 50) are integrated into a unit that receives, processes and transmits signals to and from the patient side console 1000 and surgeon side console 2000. In accordance with various embodiments, an electronics/control console as used herein also can include one or more separate controllers, e.g., processor 80, that may be provided in direct signal communication with the surgical instrument, e.g., bypassing signal communication with the patient side console. As such, a "console" does not necessarily require all controllers to be integrated into a single unit and can include one or more separate control units. Such separate controllers can be useful to add functionality to operational aspects of a surgical instrument without necessarily having to rely on servo actuators associated with the patient side console. Such controllers can also be useful when retrofitting existing robotic surgical system as a way to increase control functionality and signal processing into the electronics/control console.

Similarly, a "surgeon side console" as used herein includes a console that comprises one or more input devices that a surgeon can manipulate to transmit signals, generally through the electronics/control console, to actuate a surgical instrument interfaced with a patient side console, and one or more output devices that can provide feedback to the surgeon. As used herein, it should be understood, however, that a surgeon side console can include a unit that integrates the various input and output devices, with, for example, a display (e.g., substantially as shown by element 2000 in FIGS. 12A and 12B), but also can include separate input and/or output devices (e.g, 90 in FIG. 12A) that are in signal communication with the electronics/control console and accessible by a surgeon, although not necessarily integrated within a unit with various other input devices. As an example, input units may be provided directly at the electronics/control console and may provide input signals to a processor at the electronics/control console. As such, a "console" does not necessarily require all of the input and output devices to be integrated into a single unit and can include one or more separate input and/or output devices.

Figure 12C:
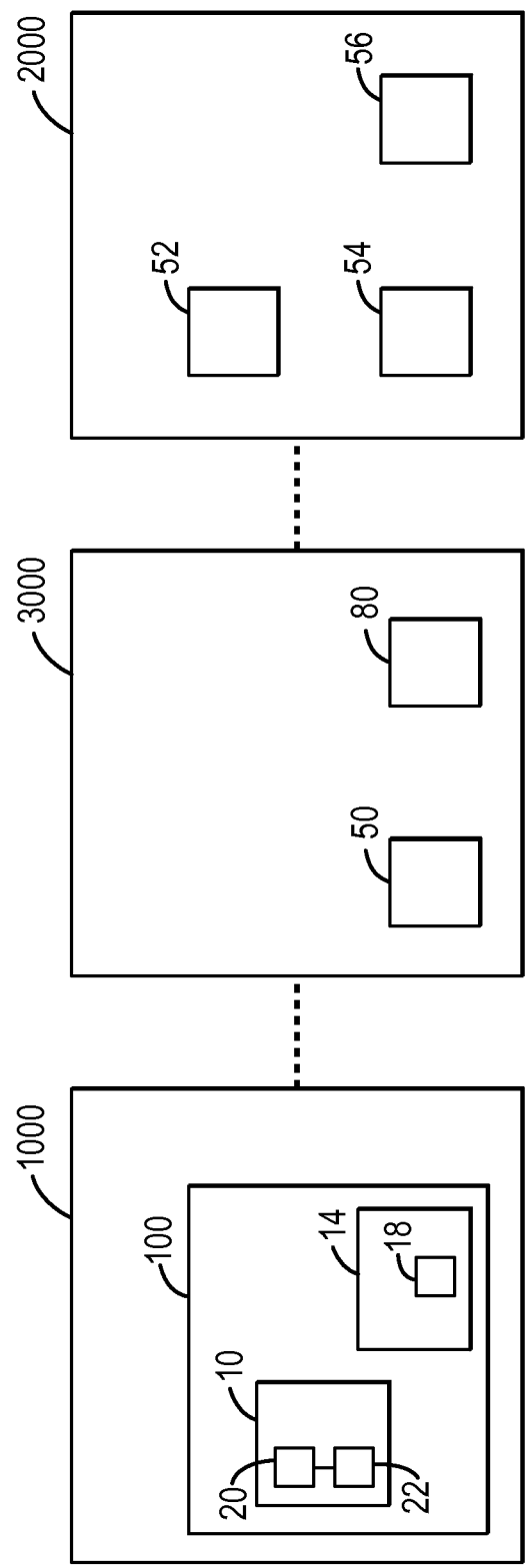
FIG. 12C is a partial schematic state diagram of the systems of FIGS. 12A and 12B according to an exemplary embodiment.

FIG. 12C is a schematic state diagram of the robotic control system showing exemplary components of a teleoperated robotic surgical system used to control the surgical instrument 100 in accordance with an exemplary embodiment of the present teachings. The electronics/control console 3000 includes at least one processor 50 that controls the operation of the surgical instrument 100 and the end effector 14. In an exemplary embodiment, the processor 50 can control the operation of a cutting blade in an exemplary embodiment of the surgical instrument end effector, or alternately, another processor 80 may directly communicate with the cutting blade, bypassing signal communication with the patient side console 1000.

The surgeon side console 2000 may include one or more input units 52 (only one being depicted for simplicity) and one or more output units 54, 56, such as, for example, a display and a speaker. In various exemplary embodiments, suitable output units may include, but are not limited to a display a speaker, (or other component capable of transmitting sound), and/or a component with which a surgeon is in contact that can vibrate or the like to provide haptic feedback. In various exemplary embodiments, the one or more output units may be part of the surgeon side console 2000 and signals can be transmitted from the core control console 3000 thereto.

As those having ordinary skill in the art are familiar with, in the case of a robotically-controlled surgical instrument 100, the transmission mechanism 10 is configured to interface with the arm of the patient side console 1000 to receive various inputs provided by servo actuators and to convert those inputs via a system of various gears, pulleys, and/or levers, etc. to forces/torques ultimately transmitted to actuate and drive the end effector to control motion thereof. In addition, as will be explained further below, the surgical instrument 100 can be in direct signal communication with the electronics/control console 3000 to provide direct drive of various drive shafts with, for example, an onboard motor disposed in the transmission mechanism 10. Of course, as described above, minimally invasive surgical instruments within the scope of the present disclosure can also be manually actuated and a proximal end transmission mechanism can instead have inputs that are manually actuated.

As will be described in further detail below, however, transmission mechanisms in accordance with various exemplary embodiments of the present disclosure can include an onboard motor, in addition to including manual and/or servo actuated inputs. Using an onboard motor in the transmission mechanism can be a relatively inexpensive way to provide additional functionality and additional degrees of freedom in the operation of a surgical instrument, for example, by driving additional movements of components of the end effector. Providing an onboard motor also can be beneficial to reduce the work needed from servo actuators in a robotic surgical system to operate an instrument.

Figure 4A:
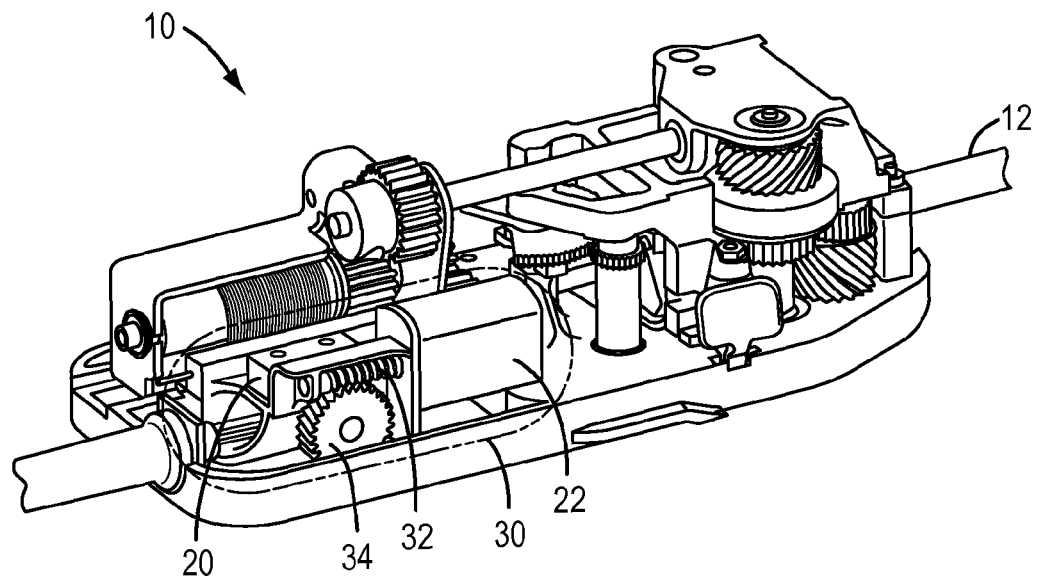
FIGS. 4A and 4B are top and bottom detailed views corresponding to the portion of the surgical instrument of FIG. 1 in accordance with an exemplary embodiment.
Figure 4B:
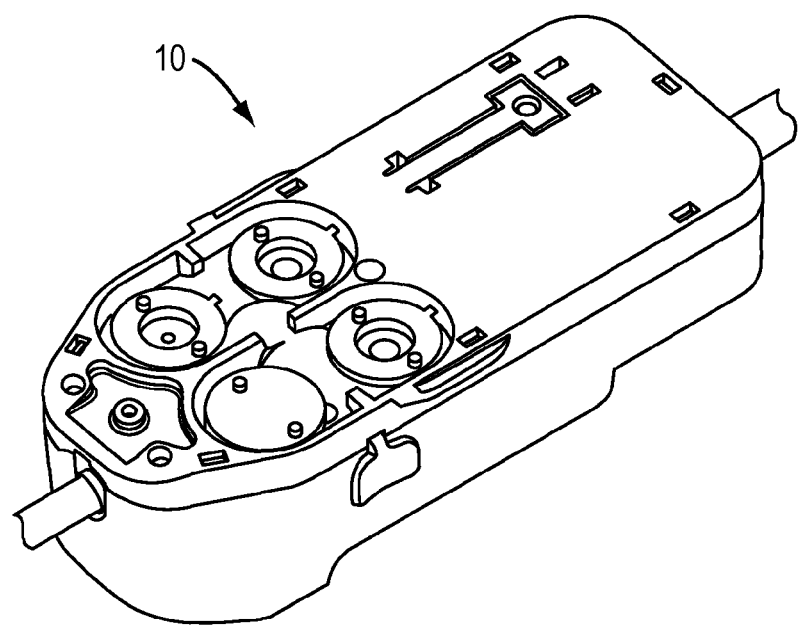
Figure 5:
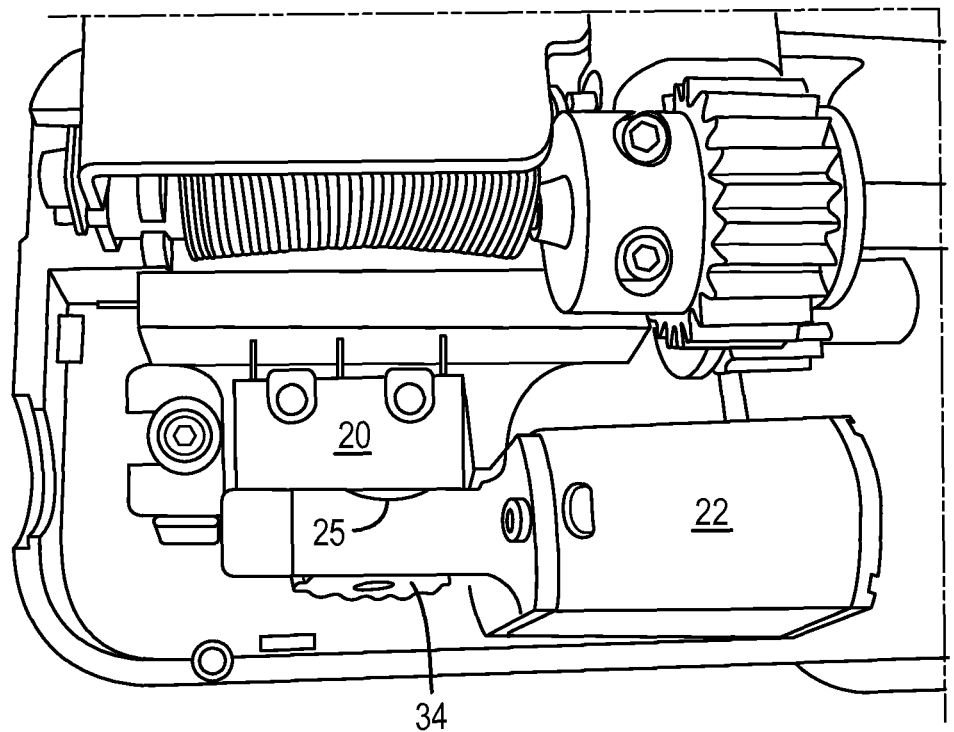
FIG. 5 is an elevation view of a portion of the transmission mechanism of FIG. 4 in accordance with an exemplary embodiment.
Figure 6:
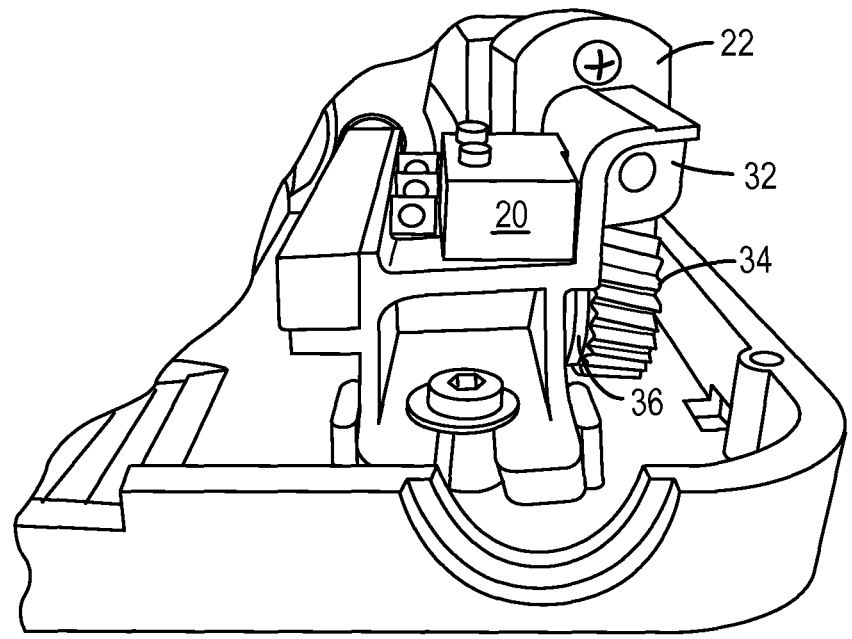
FIG. 6 is a partial rear perspective view of the portion of the transmission mechanism of FIG. 4 in accordance with an exemplary embodiment.

As will be described in further detail below, FIGS. 4A and 4B are detailed views, from top and bottom perspectives, respectively, of one exemplary embodiment of a transmission mechanism 10 (shown in FIG. 4A with its protective covering removed), corresponding generally to the detailed portion of the surgical instrument shown FIG. 1, that includes an onboard motor to drive various components of the surgical instrument in accordance with an exemplary embodiment. As will be described in further detail below, in various exemplary embodiments, utilizing the onboard motor provides a relatively robust way to drive a component of an end effector. Moreover, the use of a limit switch provides a relatively robust way to detect a position of the component as the component is driven. The ability to detect a position of the component can be useful information, for example, that can be provided to a surgeon performing a surgical procedure and/or as input that can in turn be used in a control algorithm in order to control operation of a surgical instrument.

One exemplary embodiment of a surgical instrument 100 with which aspects of the present disclosure may find particular use is a fusing and cutting surgical instrument, with the end effector 14 comprising movable jaws capable of grasping tissue therebetween and provided with electrodes to deliver electrosurgical energy to fuse the tissue, and a cutting element configured to cut the fused tissue. Such a surgical instrument relies on multiple degrees of freedom (DOF) to operate, including roll of the shaft and end effector (roll); articulation, preferably about two orthogonal directions, e.g., arbitrarily chosen "pitch" and "yaw" directions of a wrist mechanism (articulation DOF); opening and closing of the jaws (grip DOF); and translation of a cutting element relative to the end effector (translation DOF). For a further description of one exemplary embodiment of a surgical instrument configured to perform fusing and cutting operations, reference is made to U.S. patent application Ser. No. 13/399,391, entitled "FUSING AND CUTTING SURGICAL INSTRUMENT AND RELATED METHODS," filed on Feb. 17, 2012, which claims the benefit of priority to U.S. Provisional Patent Application No. 61/444,400, filed on Feb. 18, 2011 and to U.S. Provisional Patent Application No. 61/491,719, filed on May 31, 2011, the disclosures of which are incorporated herein by reference in their entireties.

Figure 3A:
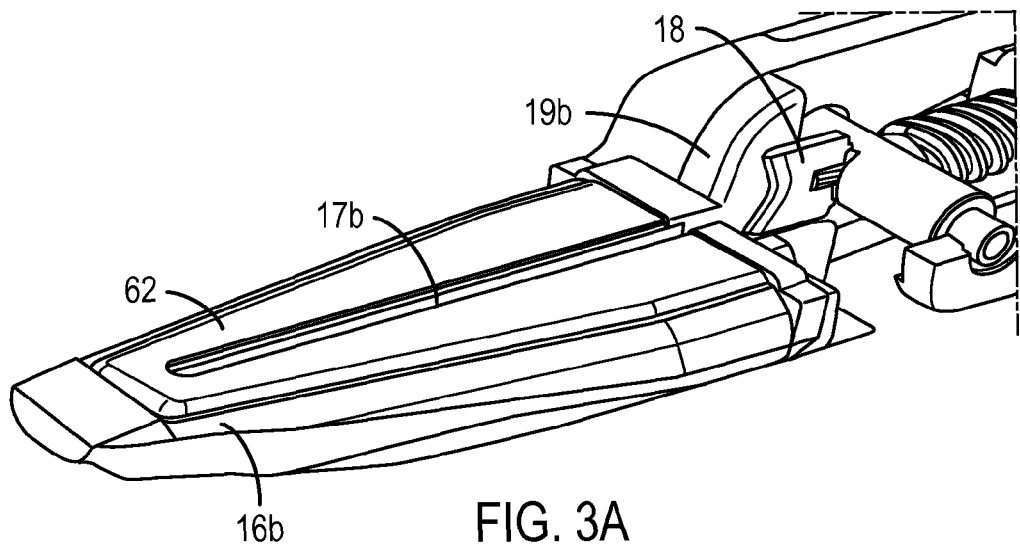
FIGS. 3A and 3B are partial perspective views of the end effector of FIG. 2 showing a cutting element respectively in a first position and a second position in accordance with an exemplary embodiment.
Figure 3B:
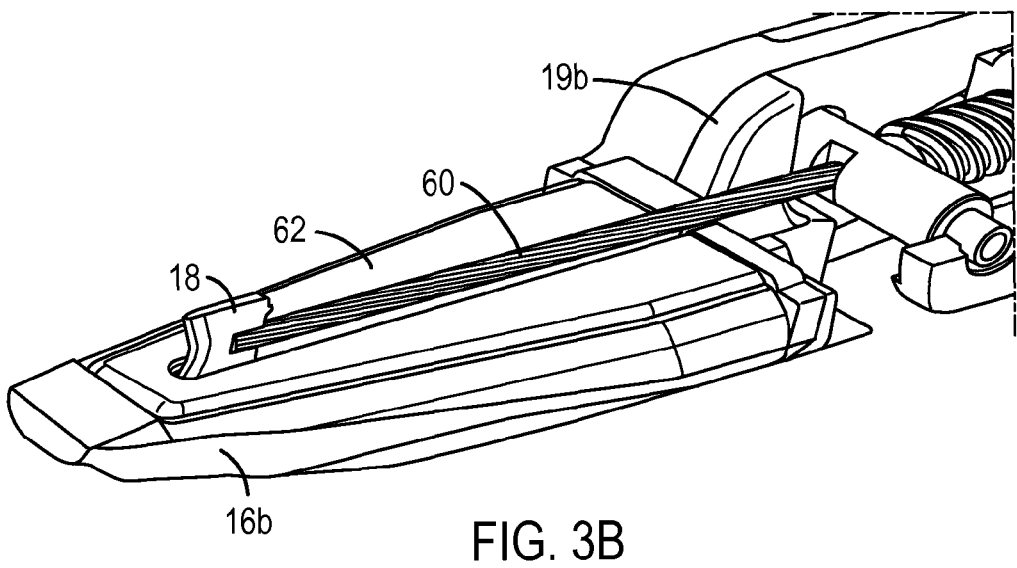
Figure 3C:
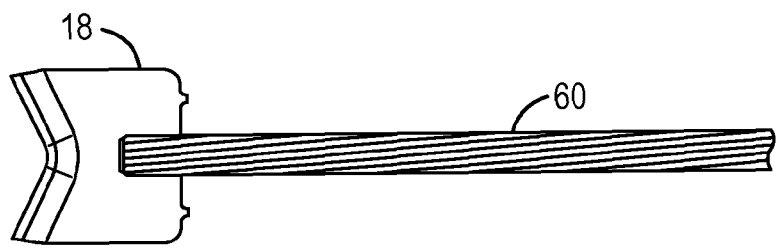
FIG. 3C is a side view of the cutting element and cutting element drive component of the end effector of FIGS. 3A and 3B in accordance with an exemplary embodiment.

FIG. 2 is a perspective view of an exemplary embodiment of an end effector 14 corresponding to a surgical instrument configured for tissue fusing and cutting. FIGS. 3A and 3B are additional perspective views of the end effector 14, with various parts thereof removed to show a better view of a cutting element, and FIG. 3C is a partial side view of the cutting element and a cutting element drive component of the end effector shown in isolation.

Briefly, the end effector 14 includes opposing upper and lower jaws 16a, 16b. The jaws 16a, 16b are configured to move between an open position and a closed position and can include electrodes 62 to provide electrosurgical energy (e.g., bipolar energy) sufficient to fuse tissue together. In addition, grooves 17a, 17b (groove 17a is hidden from view in FIG. 2) are respectively disposed along a length of each of the upper and lower jaws 16a, 16b. The end effector 14 also includes a cutting element in the form of a short cutting blade 18 (see FIGS. 3A-3C) generally disposed to move in proximal and distal directions within the grooves 17a, 17b of the jaws 16a, 16b; the grooves 17a, 17b thereby forming a track for the cutting blade 18 as the cutting blade 18 traverses along a length of the jaws 16a, 16b.

As will be discussed in more detail below, the cutting blade 18 is translated distally and proximally relative to the end effector 14. The cutting blade 18 travels between a proximal-most home position where the cutting blade 18 is in a "garaged" position in which the cutting blade 18 is recessed proximally behind the jaws 16a, 16b (see FIG. 3A), and a distal-most, fully-extended position in which the distal end of the cutting blade 18 is positioned at a distal end of the grooves 17a, 17b (see FIG. 3B). In the home ('garaged") position, the cutting blade 18 is protected by opposing garage features 19a, 19b (only 19b being shown in FIGS. 3A and 3B). The cutting blade 18 is attached to a distal end of a drive component 60, which in an exemplary embodiment can be a cable, that attaches at its proximal end to a suitable transmission mechanism, such as, for example, the transmission mechanism 10 of FIG. 4, to be actuated to extend and retract the cutting blade 18 along the track defined by the grooves 17a, 17b.

Various exemplary embodiments of the present disclosure contemplate detecting the position of the cutting blade during its translation (i.e., extension and retraction) to perform a cutting procedure. As will be explained further below, various exemplary embodiments use an onboard motor and limit switch as a robust system to detect a position of the cutting blade. In particular, various exemplary embodiments can use a detected position of the cutting blade to determine a fault condition of the cutting blade, such as, for example, to determine if the cutting blade is stuck on tissue and/or other material during the cutting procedure. Based on a determined fault condition, the operation of the cutting blade can be altered to facilitate rectifying the fault condition, for example, by altering the actuation of the cutting blade in an attempt to loosen the blade from tissue and/or other material upon which the blade is stuck.

Surgical Instrument Transmission Mechanism with Motor and Limit Switch

As described above, in accordance with one exemplary embodiment, the present disclosure contemplates a surgical instrument transmission mechanism 10 that includes a plurality of components that effect movement of the instrument shaft 12, the end effector 14, wrist 13, and/or other associated components. The transmission mechanism 10 may include a system of actuation components, such as, for example, gears, levers, gimbals, rack and pinions, pulleys, etc. to transmit inputs to the transmission mechanism 10 into various forces/torques used to drive the motion and operate the end effector 14, shaft 12, and/or wrist 13 of the surgical instrument 100. Those of ordinary skill in the art have familiarity with various configurations of transmission mechanisms provided at the proximal end of a robotically-controlled surgical instrument that are configured to interface with corresponding drive inputs provided via servo actuators on the robotic arm of the patient-side console to operate the surgical instrument. Those of ordinary skill in the art also have familiarity with a variety of transmission mechanism used in manually-actuated and controlled minimally invasive surgical instruments, including, but not limited to, for example, knobs, buttons, levers, triggers, etc.

The transmission mechanism 10 transmits received actuation inputs to resulting torques and forces to effect movement of the instrument shaft 12, the end effector 14, wrist 13, and/or associated components, to accomplish various motions resulting in a multi-DOF surgical instrument. In addition, in the depicted exemplary embodiment in accordance with an aspect of the present disclosure, the transmission mechanism 10 includes an onboard electric motor 22 that receives input voltages, for example from a robotic surgical control system (e.g., electronics/control console 3000 of FIGS. 12A and 12B), to drive the cutting blade drive component 60 via a drive system 30 that includes, for example, gears and a rack and pinion mechanism. The transmission mechanism 10 further includes a limit switch 20 that is operably coupled to the onboard motor 22. The motor 22 and limit switch 20, as well as a drive system described in further detail below, which may be removable from the transmission mechanism 10.

The motor 22 is configured to be driven by input voltages that can be provided, for example, via direct signal communication with the electronics/control console 3000, i.e., through processor 50 or processor 80, of the teleoperated robotic surgical system of FIGS. 12A and 12B, based upon received actuation inputs from the user which may be provided at inputs at the surgeon side console 2000. The motor 22 is configured to provide a driving force to a drive system 30 that is coupled with the cutting blade 18 of the end effector 14 to cause the cutting blade 18 to translate in proximal and distal directions, as discussed with reference to FIGS. 3A and 3B. The addition of the motor 22 to the transmission mechanism 10 thereby allows for an additional degree of movement, e.g., translation in proximal and distal directions of the blade 18, of the surgical instrument 100 other than the various other motions of the end effector 14, wrist 13, and/or shaft 12 of the surgical instrument. In particular, in the exemplary embodiment of FIG. 4A, in addition to roll DOF, articulation DOF, and grip DOF, which can be actuated by, for example, servo actuators associated with the patient side console 1000 of the robotic surgical system of FIGS. 12A-12B, the incorporation of the motor 22 allows for the additional movement of the cutting blade 18 without resulting in additional work for the servo actuators. Those of ordinary skill in the art will appreciate that an onboard motor can also be used with surgical instruments that are manually actuated and/or have transmission mechanisms that include both manual inputs and inputs from servo actuators.

In various exemplary embodiments, it is envisioned that the motor 22 can be used to actuate various components of the end effectors that do not require a significant amount of power to be driven, such as, for example, the translation of the cutting blade 18. Consequently, the motor 22 can be a relatively inexpensive motor, such as, for example, an off-the-shelf DC motor. Providing a relatively inexpensive motor can be beneficial for surgical instruments that are configured for single use and are disposable. Thus, in accordance with various exemplary embodiments, the entire surgical instrument 100 including a transmission mechanism 10 having the onboard motor 22 can be disposable.

In various exemplary embodiments, the motor 22 can be a DC motor configured to deliver sufficient force when operating with voltage inputs ranging from about 1 volt to about 10 volts, for example, about 6.5 volts to about 8 volts, to drive the cutting blade 18. Input voltage to the motor 22 can vary during operation of the cutting blade 18 depending, for example, on the stage of the cutting procedure. By way of example, in various exemplary embodiments, voltages may be higher when driving the blade from the home to the distal-most position and back, and may be lower during a holding of the cutting blade 18 its distal-most position during a cutting procedure. Such holding of the blade can help to prevent mechanical bouncing and allow sufficient time to complete a cutting procedure. In such a "hold" state, input voltages may range from about 1.5 V to about 4 V.

In operation using the robotic surgical system of FIGS. 12A-B, when the user (e.g., a surgeon) provides an input via the surgeon side console 2000 to, for example, perform a cutting operation, in response to the user input, the electronics/control console 3000 outputs voltage to the motor 22 at the transmission mechanism 10 in order to cause operation of the motor 22. When voltage is provided to the motor 22 from the electronics/control console 3000 in response to the input at the surgeon side console 2000, the motor 22 is configured to provide driving force to components in the transmission mechanism to operate the cutting element drive component 60 attached to the cutting blade 18 to cause the cutting blade 18 to extend distally or retract proximally.

Figure 13:
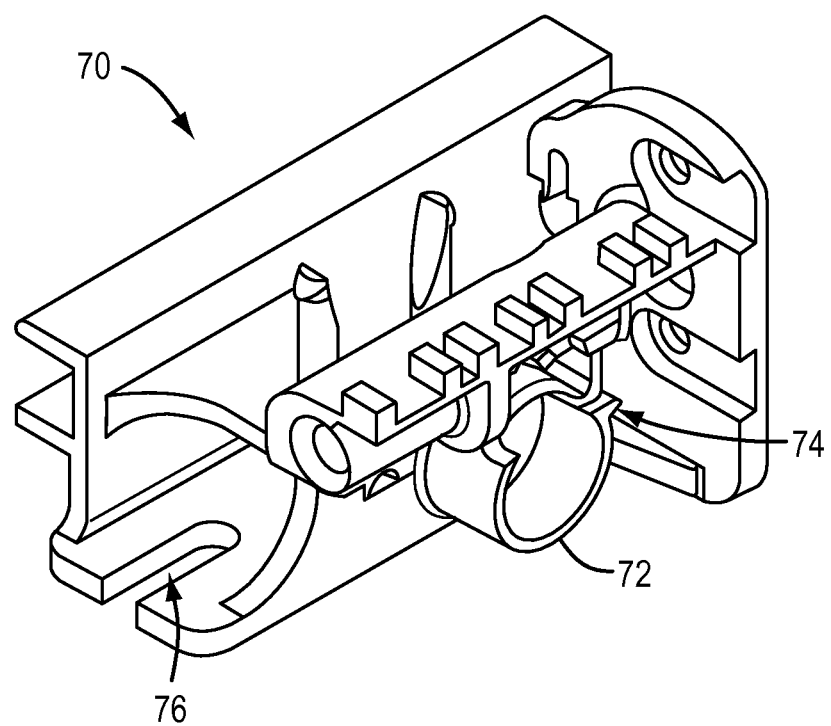
FIG. 13 is a perspective view of a chassis of the transmission mechanism of FIG. 4 shown in isolation in accordance with at least one exemplary embodiment.

In one exemplary embodiment as depicted in the various views of FIGS. 4-8, the drive system 30 can include a worm shaft 32 that is directly coupled to the drive shaft of the motor 22 and rotated therewith. The worm shaft 32 in turn engages with a worm gear 34 of a reduction gear component 33 (shown in isolation in FIG. 8). As shown best in FIG. 8, the reduction gear component 33 includes a shaft 35 with the worm gear 34 attached to one end and a pinion gear 36 (having a smaller diameter than the worm gear 34) attached at the opposite end. The worm gear 34 and the pinion gear 36 thus rotate together about the longitudinal axis of the shaft 35. The worm gear 34 is received within a cylindrical gear receptacle 72 of a chassis 70 of the transmission mechanism 10 (shown in isolation in FIG. 13). With reference now to FIGS. 7A-7B and 9A-9B, the pinion gear 36 engages with a rack 40 to which the drive component 60 for the cutting blade 18 is secured for movement therewith. In an exemplary embodiment, the drive component 60 could be, for example, a cable or a cable crimped to a tubing, e.g., a hypotube, terminating at a proximal end of the instrument 100 along a portion of the shaft 12 of the instrument 100. The rotation of the pinion gear 36 causes the movement of the rack 40 in the proximal and distal directions with respect to the end effector 14, which in turn results in push/pull forces being exerted on the drive component 60. The drive component 60 rotates relative to rack 40, and may rotate along with shaft 12 of the instrument 100. The cutting element drive component 60 is routed from the transmission mechanism 10 along the length of the shaft 12, through the wrist 13 (if any) of the surgical instrument 100 and terminates at the end effector 14 where the cutting element drive component 60 is attached to the cutting blade 18. The movement of the cutting element drive component 60 causes translation of the attached cutting blade 18 in the distal and proximal directions along the grooves 17a, 17b of the jaws 16a, 16b as described above. FIG. 9A shows the drive system 30 and cutting element drive component 60 corresponding to a fully-extended, distal-most position of the cutting blade relative to the jaws 16a, 16b of the end effector 14, while FIG. 9B shows the drive system 30 and cutting element drive component 60 corresponding to a fully-retracted, proximal-most position of the cutting blade 18 relative to the jaws 16a, 16b.

Figure 7A:
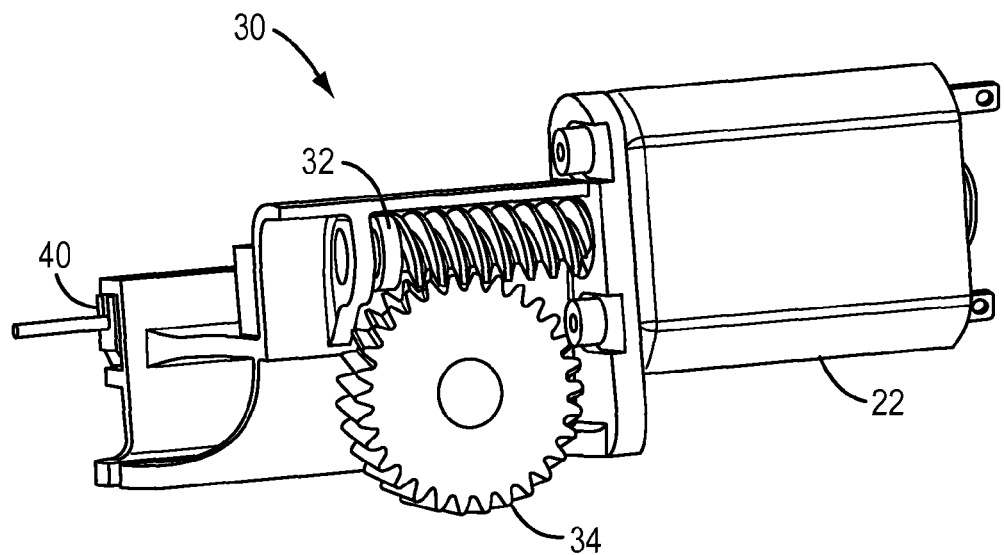
FIGS. 7A-7B are differing perspective views of a drive system in cooperation with a motor and a portion of a chassis of the transmission mechanism of FIG. 4.
Figure 7B:
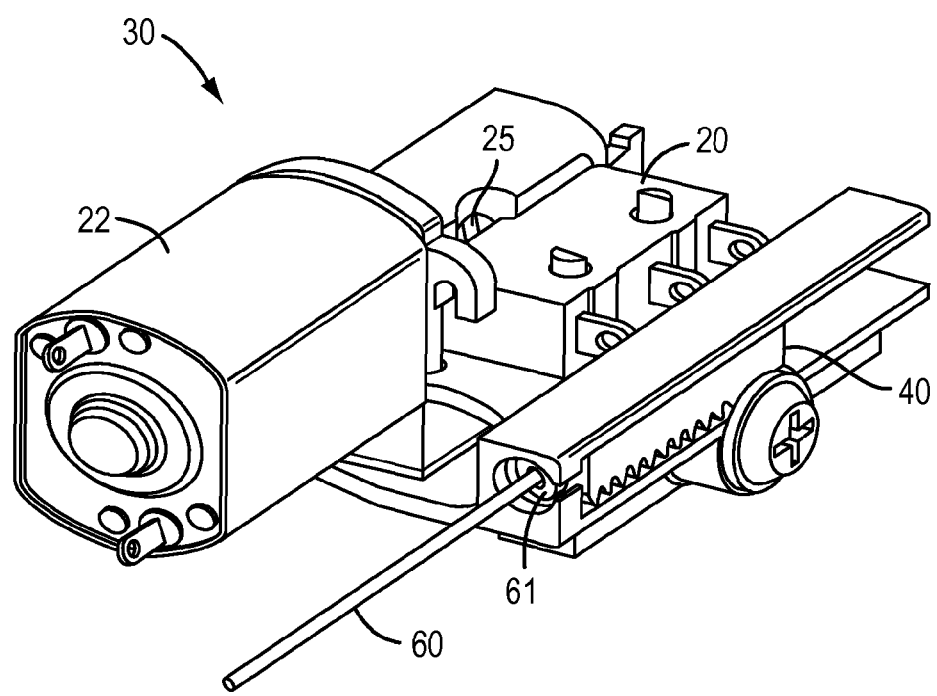

A bearing 61 may be provided distal to the rack 40 in the chassis 70 (shown in FIG. 7B, for example). A lead-screw assembly (not shown), including, for example, a screw, a flexible coil to bend at the wrist 13, and a tube extending from distal to proximal ends, that is used to open and close the jaws 16a, 16b is positioned proximate to the chassis 70 against the bearing 61. When the jaws 16a, 16b are opened, the bearing 61 supports an axial thrust load of the lead-screw assembly as the assembly moves in the direction of the chassis 70. When the jaws are closed, the screw moves forward and does not exert a load on the bearing 61. For further details regarding use of a lead-screw assembly for opening and closing the jaws of an end effector, reference is made to U.S. patent application Ser. No. 13/399,391, entitled "FUSING AND CUTTING SURGICAL INSTRUMENT AND RELATED METHODS," filed on Feb. 17, 2012, which claims the benefit of priority to U.S. Provisional Patent Application No. 61/444, 400, filed on Feb. 18, 2011 and to U.S. Provisional Patent Application No. 61/491,719, filed on May 31, 2011, the disclosures of which are incorporated herein by reference in their entireties.

Those having ordinary skill in the art will appreciate that the drive system 30 disclosed herein is nonlimiting and exemplary only, and any of a variety of other systems can be used to operably couple the motor 22 with the cutting element drive component 60 to cause the rotary shaft motion of the motor to be converted to the linear push/pull movement of the drive component 60, and thereby translation of the cutting blade 18 in proximal and distal directions.

The drive system 30 also includes a chassis 70 (shown in isolation in FIG. 13) to protect and join together the various components of the drive system 30. The chassis 70 permits the entire drive system 30, along with motor 22 and limit switch 20, to be relatively easily secured to and removed from various housing parts (shown in at least some of the illustrations depicting the drive system 30) of the transmission mechanism 10, for example, by using one or more screws, bolts, etc. between the chassis 70 and the transmission mechanism housing engaging the chassis 70 at a screw slot 76. The separate attachment of the drive system 30 as an assembly allows for an accommodation for tolerance stack-ups of individual parts of the instrument 100 to approximately ±3/32 inches.

As mentioned above, in some cases it may be desirable to obtain information about the position of a translating component of an end effector during its operation. In various exemplary embodiments, a limit switch can be used in conjunction with a translating component of an end effector to provide such position information regarding the position of the translating component. For example, as shown with particular reference to FIGS. 5, 6, 7B, 9A, and 9B, in various exemplary embodiments, a limit switch 20 can be utilized in conjunction with the motor 22 and drive system 30 to provide position information of the cutting blade 18 as the blade 18 translates relative to the jaws 16a, 16b of the end effector 14.

As shown, the limit switch 20 includes a component, such as a button 25, which is able to be depressed and released from a depressed state. The limit switch 20 may be provided in any of a variety of positions in the transmission mechanism 10 that permits the component, e.g., button 25, of the limit switch 20 to be depressed or released based on inputs from the actuation of the motor 22. As shown in FIGS. 9A and 9B, for example, the limit switch 20 is provided so as to engage with the worm gear 34 of the drive system 30, as will be explained in further detail below. Such positioning and operation of the limit switch is nonlimiting and exemplary only, however, and other arrangements may be used as would be apparent to those having ordinary skill in the art to cause actuation of the limit switch as the cutting element translates. For example, in an exemplary embodiment, a rack may directly activate the limit switch 20 based on the linear movement of the rack as the cutting element translates. A cam attached to the rack, for example, may contact the limit switch 20, which activates the limit switch 20 based on the linear movement of the rack.

Figure 8:
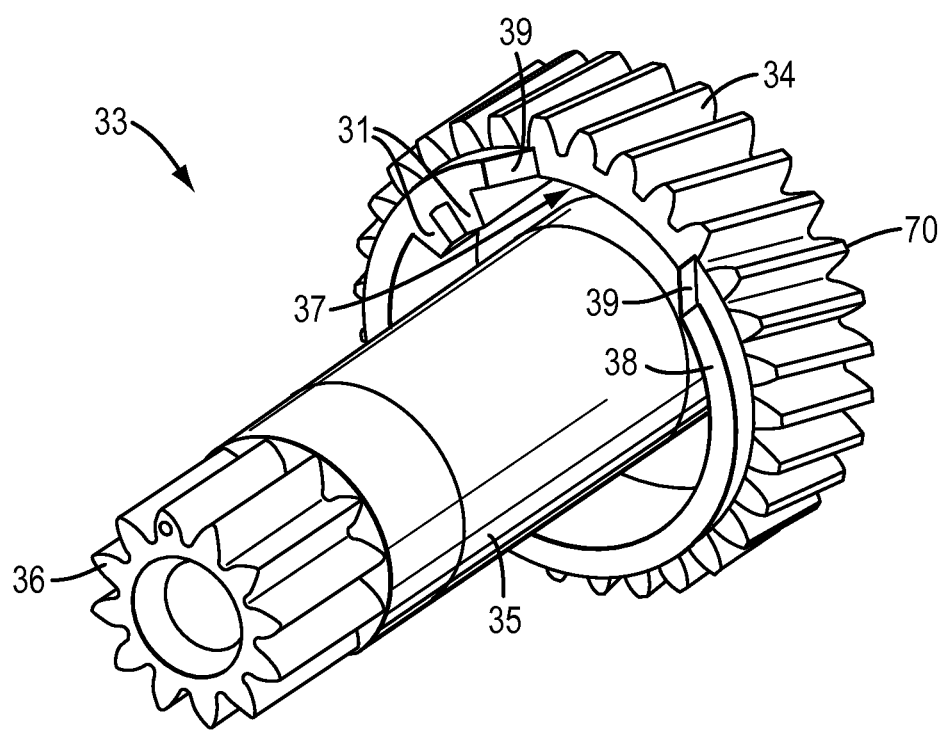
FIG. 8 is a perspective view of a gear component of the drive system of FIGS. 7A and 7B shown in isolation in accordance with an exemplary embodiment.
Figure 9A:
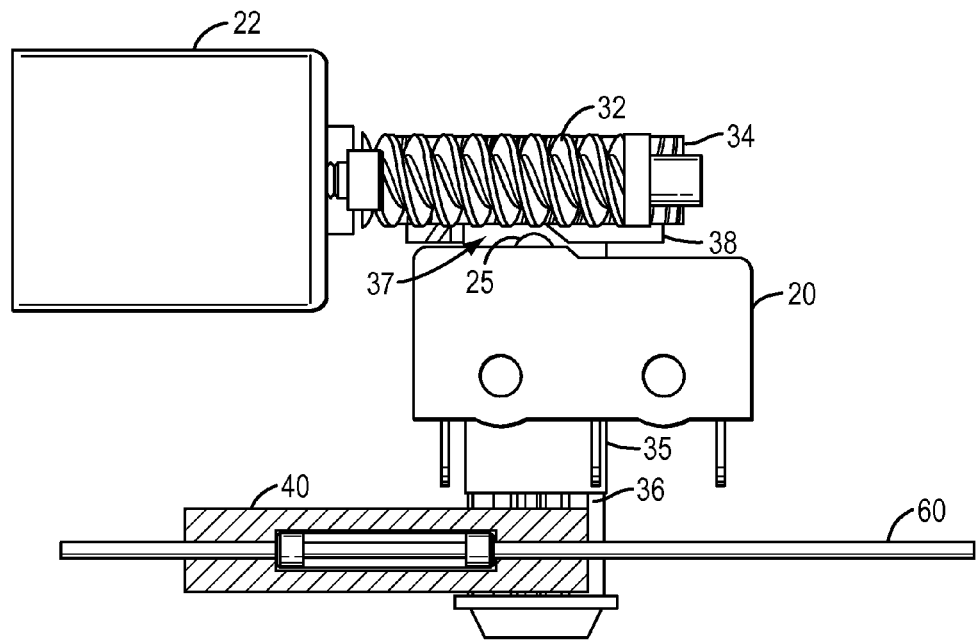
FIGS. 9A and 9B are partial elevation views of the motor and drive system of FIGS. 7A and 7B shown with the drive component of a cutting element of a surgical instrument in a fully-extended, distal-most position and a fully-retracted, proximal-most position, respectively.
Figure 9B:
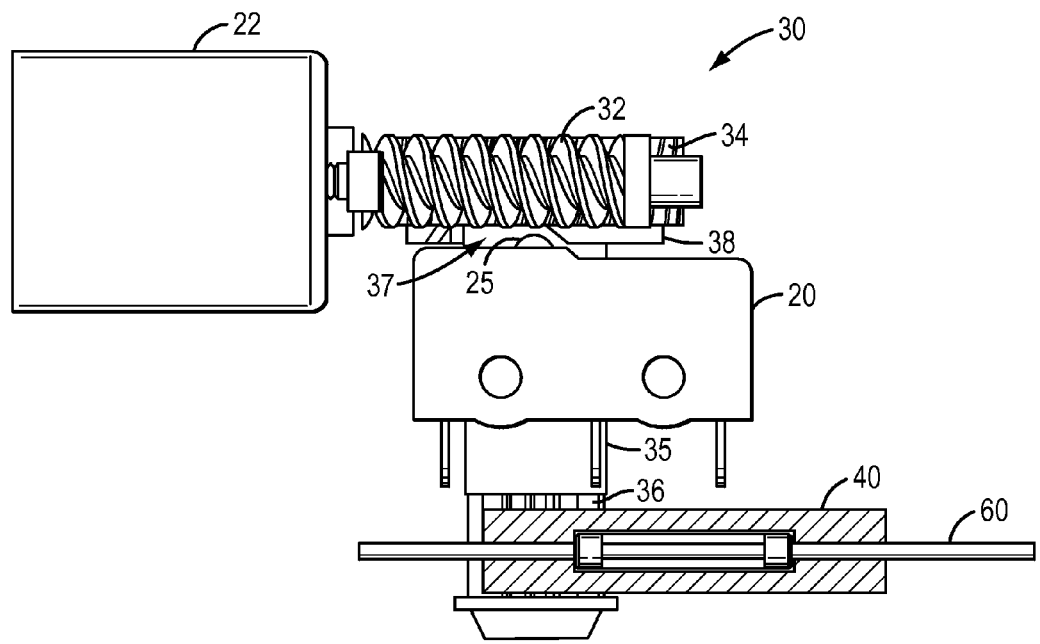

With reference to FIGS. 8, 9A and 9B, the worm gear 34 includes a flange 38 that extends from an internal surface of the gear 34 in a direction slightly along the shaft 35. The flange 38 extends partially around a circumference of the internal surface of the worm gear 34 and terminates at two ends 39. A notch 37 is defined between the two ends 39 of the flange 38, i.e., along the portion of the internal surface of the worm gear 34 where the flange 38 does not extend. In an initial position of the worm gear 34, corresponding to the home, "garaged" position of the cutting blade 18 attached to the drive component 60, the button 25 of the limit switch 20 is maintained within the notch 37 out of contact with the flange 38 and in a released state. As the worm gear 34 rotates to move the drive component 60 (and consequently to translate the cutting blade 18 relative to the jaws 16a, 16b), the button 25 engages with the flange 38 and is thereby depressed as the drive component 60 is concurrently being moved. The angular extent of the flange 38 corresponds to the distance of travel to move the cutting blade 18 from its home (garaged) position to its distal-most, fully extended position. Accordingly, when the drive component 60 has moved to a position corresponding to the cutting blade 18 being in its fully extended, distal-most position, and the worm gear 34 has rotated almost 360 degrees, the button 25 is released from the extension flange 38 back into the notch 37 (at the opposite side from where it started in the home, garaged position) and out of contact with the extension flange 38. A stop portion 31 extends inwardly from the flange 38 toward the shaft 35 and abut against a stop-engaging portion 74 of the gear receptacle 72 at the home position and the fully extended position, which stops the rotation of the worm gear 34, thus limiting the movement of the worm gear 34 and the corresponding movement of the drive component 60. While the stop portion 31 is shown proximate to the notch 37 in FIG. 8, one of ordinary skill in the art would recognize that the stop portion 31 may be at any position on the flange 38 that allows for engagement against the stop-engaging portion 74 of the gear receptacle 72.

Thus, the button 25 moves from a released, undepressed state, to a depressed state and then to a released, undepressed state. After reaching its fully extended, distal-most state, the motor 22 can be driven in the opposite direction to retract the cutting blade 18 and return the blade 18 to its garaged position. In doing so, the reverse rotation of the worm gear 34 again causes the flange 38 to engage and depress the button 25 on the limit switch 20 as the blade 18 and drive component 60 are translated from the distal-most position to the proximal-most, garaged position. Again, upon reaching the garaged position of the cutting blade 18, the button 25 is positioned back in the notch 37 where the button 25 started, and released from the depressed state out of contact with the flange 38. Thus, the flange 38 acts as a cam to depress and release the button 25 provided on the limit switch 20 as the worm gear 34 rotates to translate the drive component 60.

With reference to FIGS. 3A and 3B, the cutting element drive component 60 moves the cutting blade 18 between a home (garaged) position in which the cutting blade 18 is retracted from the end effector 14 (FIG. 3A) and a fully-extended position in which the cutting blade 18 is fully-extended within the track defined by grooves 17a, 17b (FIG. 3B). Thus, as the worm gear 34 begins moving, causing the movement of the cutting blade 18 along the track defined by the grooves 17a, 17b, the button 25 of the limit switch 20 is depressed. When the worm gear 34 is either in the initial position in which the button 25 of the limit switch 20 is received within the notch 37 or is in a fully-rotated state (corresponding to a fully-extended position of the cable 60 and cutting blade 18) in which the button 25 is received within the notch 37, then the button 25 is in a released state.

Therefore, as the rotation of the worm gear 34 is connected with the extension of the cutting element drive component 60, and thereby the position of the cutting blade 18, and also is connected with the depression of the limit switch component, e.g., button 25, then the position of the cutting blade 18 is associated with the depression of the limit switch component, e.g., button 25. In particular, when the cutting blade 18 is fully-retracted into the home, garaged position (FIG. 3A) or fully-extended into a fully-operational position (FIG. 3B), then the limit switch component, e.g., button 25, is released within the notch 37. When the cutting blade 18 is moving from the home position or the fully-operational position, either from the home position toward the fully-operational position or from the fully-operational position to the home position, then the limit switch component, e.g., button 25, becomes depressed. The depression or release of the limit switch button 25, or the altering of some other component associated with the limit switch 20, either closes or opens the electrical circuit of the limit switch 20, as those of ordinary skill in the art are familiar with. Closing or opening the electrical circuit in turn provides (or interrupts) an electrical signal indicating either that the drive component 60 and cutting blade 18 are translating between the home and fully extended positions, or are in one of the home or fully extended positions.

In an exemplary embodiment in which the surgical instrument 100 is used with a teleoperated robotic surgical system such as that in FIGS. 12A-12B, the limit switch 20 can be provided in electrical signal communication with the electronics/control console 3000 to provide position information thereto, and the electronics/control console 3000 can in turn use that information to perform various control operations over the surgical instrument and/or to provide position feedback information to a surgeon at the surgeon side console 2000.

Although it is discussed above that the button 25 of the limit switch 20 is depressed when the cutting blade 18 is moving (translating) between the home position and the fully-operational position and is released when the cutting blade 18 is in the home position and in the fully-operational position, one of ordinary skill in the art would recognize that a component (such as, e.g., button 25) of the limit switch 20 can instead be in a released, undepressed state while the cutting blade 18 is moving and depressed when the cutting blade 18 is in either the home position or the fully extended position. However, the button 25 may preferably be depressed, and thus the limit switch 20 in an actuated state, when the button 25 is moving along the flange 38 when the blade 18 is translating between the home position and the fully-extended position because the motor 22 would just be coming up to speed when the motor 22 causes the actuation of the limit switch 20, so the dynamic (impact) loads on a switch plunger (not shown) would be less, which would mean less wear and tear on the limit switch 20. Further, as above, the mechanism that triggers the limit switch 20 to either open or close the electrical circuit of the limit switch need not be a depressable button, but could be a variety of mechanisms that can be moved from a first configuration to a second configuration to open and close the switch 20. Suitable mechanisms can include, but are not limited to, for example, toggle mechanisms, sliding mechanisms, rotating mechanisms (e.g., knobs), etc.

Although the above description described use of a motor and limit switch to control the operation and detect positioning of a cutting element of a surgical instrument end effector, those of ordinary skill in the art will appreciate that other surgical instrument end effector components could be similarly controlled and their position detected. For example, the above-described embodiments of the motor, drive system, and/or limit switch could be implemented in a variety of surgical instruments to control an end effector, including, but not limited to, for example, a surgical stapling instrument having a cutting mechanism, etc.

Surgical Instrument with Control for Detected Fault Condition

As mentioned above, aspects of the present disclosure further contemplate providing control over a surgical instrument end effector to automatically attempt to rectify a detected fault condition during the operation of the same. In various exemplary embodiments in accordance with the present disclosure, control over the cutting blade 18 of the surgical instrument 100 is contemplated, for example, to release the cutting blade 18 in the event the blade 18 becomes stuck (e.g., on tissue or other material) during a cutting procedure. In at least one exemplary embodiment, described in more detail below, the position information, for example, obtained by the limit switch 20, can be used to detect a fault condition of the cutting blade 18 and control operation of the same based on the detected fault condition.

Figure 10:
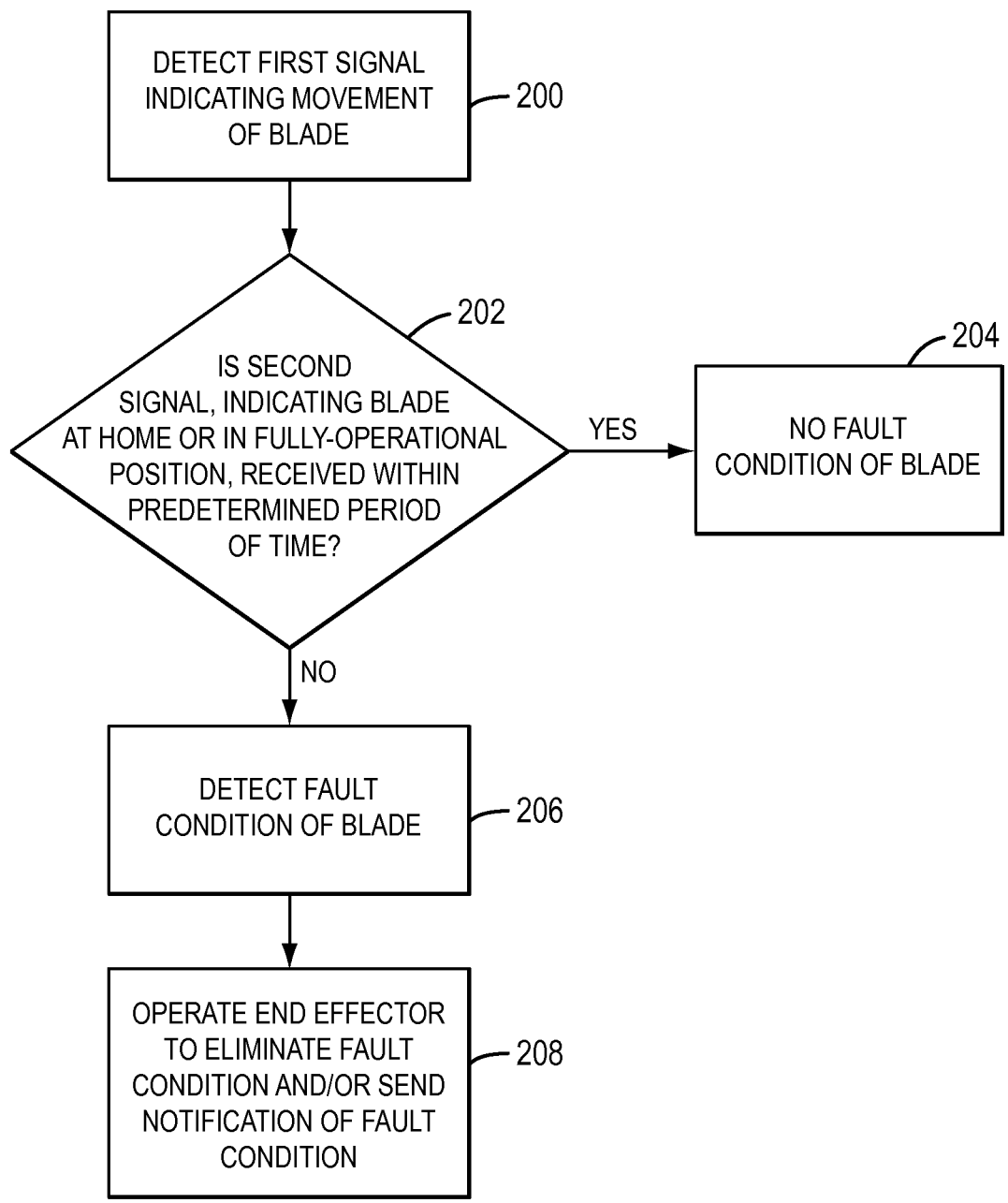
FIG. 10 is a flow diagram illustrating an exemplary method of detecting a fault condition of an end effector component of the robotically-controlled surgical instrument in accordance with at least one exemplary embodiment.

FIG. 10 is a flow diagram illustrating an exemplary method of controlling an end effector of a surgical instrument in accordance with at least one exemplary embodiment of the present disclosure. As above, in at least one exemplary embodiment, the exemplary method of FIG. 10 can be employed in operating a fusing and cutting surgical instrument, such as, for example, that described in U.S. patent application Ser. No. 13/399,391, entitled "FUSING AND CUTTING SURGICAL INSTRUMENT AND RELATED METHODS," filed on Feb. 17, 2012, which claims the benefit of priority to U.S. Provisional Patent Application No. 61/444,400, filed on Feb. 18, 2011 and to U.S. Provisional Patent Application No. 61/491,719, filed on May 31, 2011, the disclosures of which are incorporated herein by reference in their entireties.

In an exemplary embodiment, the control method may be implemented in a teleoperated robotic surgical system such as that illustrated in FIGS. 12A-B, and the method of FIG. 10 also will be described in conjunction with the use of a motor/limit switch for position detection as described above with reference to the exemplary embodiments of FIGS. 4-9. As shown in FIG. 10, at operation 200, a first signal is received, for example, by the electronics/control console 3000, which indicates that the cutting blade 18 of the end effector 14 is translating from one of a home position and a fully-operational position. As described above, the signal may be provided through the use of a limit switch, the state of which corresponds to a position of the cutting blade 18. Further, as discussed above, when the user (e.g., surgeon) provides input via one or more input devices 52 at the surgeon side console 2000 to actuate the surgical instrument to perform a cutting operation, an input signal is transmitted to the electronics/control console 3000. With reference to the motor/limit switch embodiments described above, the electronics/control console 3000 in turn can provide voltage to the motor 22 at the transmission mechanism 10. The motor 22 provides a driving force to the drive system 30, which causes the button 25 of the limit switch 20 to be depressed. When the button 25 is depressed, indicating that the cutting blade 18 is moving from either the home position or the fully-operational position, which may be, for example, a fully-extended, distal-most position of the cutting blade 18 within the track defined by grooves 17a, 17b, then the limit switch 20 outputs a first signal that is detected at the electronics/control console 3000. The signal output by the limit switch 20 can either be an electrical signal produced by closing a circuit of the switch 20, or can be the interruption of an electrical signal produced by opening the circuit.

Although various embodiments use a single limit switch 20, it is envisioned that two limit switches could be used to detect proximal and distal positions of the cutting blade 18.

The input device(s) 52 of the surgeon side console 2000 can be one or more of a variety of input devices, including, but not limited to, foot pedals, grips, buttons, keyboards, mouse components, speakers configured to operate in conjunction with voice recognition software, joysticks, etc.

It is to be understood by one of ordinary skill in the art that the fully-operational position is not limited to a fully-extended position of the cutting blade 18 at the distal end of the grooves 17a, 17b shown in FIGS. 2 and 3, but may be any position of the cutting blade 18 along the track defined by grooves 17a, 17b that corresponds with a position of the notch 37 at an end of the flange 38 of the worm gear 34. Further, more than one notch 37 can be provided along a length of the flange 38 to correspond to predetermined positions of the end effector component, e.g., cutting blade 18, that it may be desirable to be aware of during an operation utilizing a translating end effector component.

At operation 202, the electronics/control console 3000 determines whether a second signal is received from the limit switch 20 indicating that the cutting blade 18 is in one of the home position or the fully-operational position. As discussed above, when the worm gear 34 rotates to a predetermined position, the limit switch component, e.g., button 25, is received within a notch 37 of the worm gear 34, which releases the button 25 from the depressed state and out of contact with the flange 38. As the drive component 60, which controls the position of the cutting blade 18, is controlled in concert with the rotation of the worm gear 34, when the button 25 is received in the notch 37, then the released (undepressed) state of the button 25 indicates that the cutting blade 18 is either in the home position or in the second (e.g., fully-extended) position. When the button 25 is released, the limit switch 20 outputs a second signal that is received at the core control console 3000.

At operation 202, the electronics/control console 3000 determines whether the second signal is received within a predetermined time period after detecting the first signal. When the second signal is received within the predetermined time period after the first signal is detected, at operation 204, the electronics/control console 3000 does not detect a fault condition of the cutting blade 18. If the predetermined time period after the first signal is detected elapses without receiving the second signal at the electronics/control console 3000, then a fault condition of the cutting blade 18 is detected at operation 206. For example, the fault condition of the cutting blade 18 indicates, for example, that the blade 18 is stuck (e.g., on tissue or other material) and unable to return to the home position.

In various exemplary embodiments, the predetermined time period above can range from about 500 ms to about 1000 ms. Further, the predetermined time period may be a total period of time sufficient to advance the cutting blade 18 from a home position to a fully-operational position in which, for example, the cutting blade 18 is fully-extended to perform a cutting procedure, and to fully retract back to the home position. The predetermined time period may be, for example, a total of 1000 ms, from when the cutting blade 18 begins moving from the home position to the fully-operational position and reaches the fully-operational position at which cutting occurs, e.g., 500 ms, and moves back to the home position from the fully-operational position, e.g., 500 ms. In this case, the second signal that is received is a signal indicating that the cutting blade 18 has retracted to the home position and the limit switch therefore moves from a depressed state (during translation of the cutting blade from the home position), to an undepressed state (at the fully-extended position of the cutting blade), back to a depressed state (during retraction of the cutting blade from the fully-extended position), and back to an undepressed state (at the home position of the cutting blade). In an alternative embodiment, the predetermined time period is a period of time, for example, 500 ms, from when the cutting blade 18 begins moving from the home position to when the cutting blade 18 reaches the fully-operational (e.g., fully-extended) position. In this case, the second signal that is received is a signal indicating that the cutting blade 18 has reached the fully-operational position. In another alternative, the predetermined time period is a period of time, for example, 500 ms, from when the cutting blade begins moving from the fully-operational position to when the cutting blade 18 reaches the home position. In this case, the second signal that is received is a signal indicating that the cutting blade 18 has retracted to the home position.

At operation 208, when the fault condition of the end effector component, such as cutting blade 18, is detected, then the electronics/control console 3000 sends control signals to automatically actuate the end effector 14 in an attempt to rectify the fault condition and/or a notification signal is transmitted, for example, to the surgeon side console 2000 or elsewhere, to output to the user an indication of the fault condition of the end effector component. A notification may be transmitted alone or may be transmitted as the end effector is operated to eliminate the fault condition. One or more notification signals may be transmitted from the electronics/ control console 3000 that detects the fault condition of the cutting blade 18 to one or more output units 54, 56, e.g., display 54 and/or speaker 56, at the surgeon side console 2000. The notification signal can cause any of a variety of perceptible feedbacks to the user (e.g., surgeon), including but not limited to visual feedback, such as, for example, an image, text, and/or an icon presented on a display; audio feedback (e.g., a beep, buzz, chime, click, etc., or computer-generated voice response, etc.); haptic sensation (e.g., vibration) feedback, or combinations thereof.

At operation 208, either separately from transmitting the notification signal or concurrently therewith, the end effector 14 can be automatically operated based on signals from the electronics/control console 3000 to eliminate the fault condition. For example, during the automatic operation of the end effector 14, the electronics/control console 3000 may not respond to some inputs from the surgeon side console 2000, such as, for example, a pedal input devices configured to control a cutting operation of the end effector 14. Though it is envisioned that override control can still be provided at the surgeon side console 2000. In an exemplary embodiment, operation 208 can include sending a signal from the electronics/control console 3000 to the patient side console 1000 to move the jaws 16a, 16b to open a predetermined distance in order to attempt to free the cutting blade 18 from the material on which it is stuck. The jaws 16a, 16b may be fully opened or opened to a limited degree in order to aid in releasing the cutting blade 18 from tissue to which the blade 18 is attached.

Figure 11:
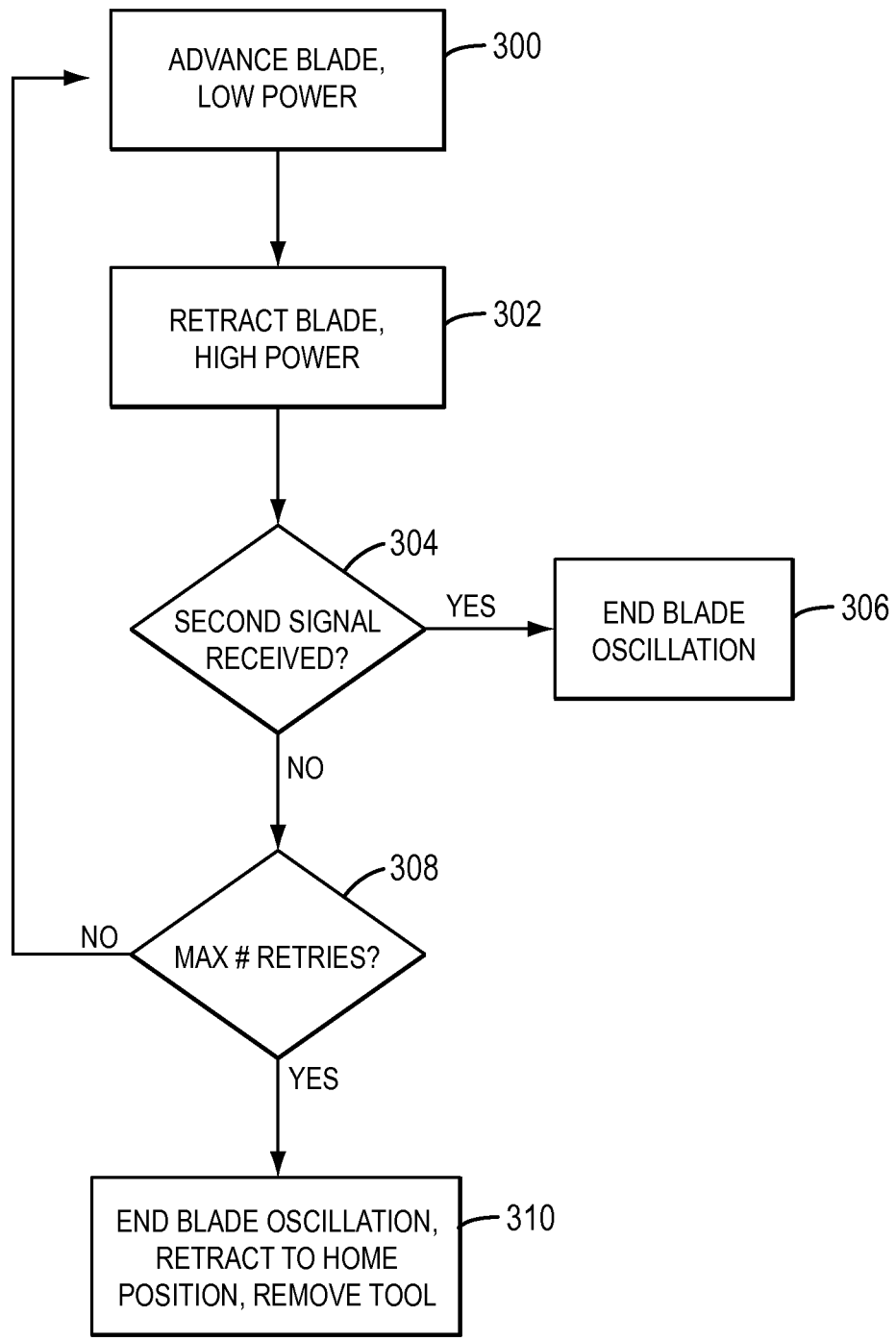
FIG. 11 is a flow diagram illustrating an exemplary method of controlling an end effector component of the robotically-controlled surgical instrument in accordance with at least one exemplary embodiment.

In another alternative, either in lieu of, concurrently with, or subsequent to opening of the jaws, the cutting blade 18 can be automatically operated and motion imparted thereto in an attempt to loosen it from the material upon which it is stuck. Turning now to FIG. 11, an exemplary method for automatically operating the cutting blade 18 to attempt to free it from a stuck condition is depicted. In the exemplary method of FIG. 11, the cutting blade 18 may be subjected to a back and forth (e.g., oscillatory) movement. At operation 300 in FIG. 11, the drive component 60 of the cutting blade 18 is actuated to be advanced toward the fully-operational position of the blade 18. At operation 302, the drive component 60 is subjected to an actuation force to retract the cutting blade 18 toward the home position. In an exemplary embodiment, the actuation force used at operation 302 can be larger than the force at operation 300. The larger driving force at operation 302 may be desirable to cause the cutting blade 18 to be released from the tissue to which the blade 18 is stuck while the actuation force acting on the cutting element drive component 60 is a force moving the component 60 in a retraction direction. Providing a greater driving force in the proximal (retraction) direction than the driving force in the distal (extension) direction can assist in preventing the blade 18 from becoming stuck in a more extended position, Further, this can also assist to bias the force in the proximal (retraction) direction so that the blade 18 may ultimately move closer to the home position with each oscillation.

If the second signal is received at operation 304, then the blade 18 has been received at one of the home position or the fully-operational position, indicating that the blade 18 has been released from the tissue. The blade oscillation is thus ended at operation 306 when the second signal is received. If the second signal is not received at operation 304, then operations 300 and 302 of the oscillation are performed for a predetermined number of cycles, until a maximum number of oscillation cycles is met at operation 308. If a maximum number of oscillation cycles has been met, indicating that the blade 18 is still stuck, at operation 310, the blade oscillation operation ends. At this point, the user (e.g., surgeon) is permitted to attempt to remove the entire surgical instrument 100 from the patient and/or to perform another procedure (e.g., using inputs at the surgeon side console 2000) to attempt to remove the cutting blade from its stuck condition.

The oscillatory operation of the cutting blade 18 can be performed using the onboard motor 22 and drive system 30 shown and described above with reference to FIGS. 4-9. In an exemplary embodiment, the motor 22 can be operated to drive the cutting blade 18 distally for at least about 30 ms, e.g., about 125 ms, hold the cutting blade 18 in the distal position for about 100 ms, and then drive the cutting blade 18 proximally for at least about 30 ms, e.g., about 125 ms. For example, the total cycle period may be about 350 ms, for example. In an exemplary embodiment, the voltage applied to the motor 22 can range from about 2.5V to about 8V, e.g., from about 6.5V to about 8 V, to actuate the drive component 60 to advance the cutting blade 18 in the distal direction. In an exemplary embodiment, the voltage applied to the motor 22 can range from about 2.5V to about 8V, e.g., from about 6.5V to about 8V, to actuate the drive component 60 to retract the cutting blade 18 in the proximal direction.

Those having ordinary skill in the art would appreciate that the operations shown and described above with reference to FIGS. 10 and 11 are not limited to use of an onboard motor in a transmission mechanism as the mechanism to provide the motive force to operate the end effector to release the stuck component (e.g., cutting blade 18), and the same operations could be used with servo actuators interfacing with the transmission mechanism to control the end effector operation. Moreover, the operations of FIGS. 10 and 11 could be implemented on a variety of surgical instruments having configurations other than the specific embodiments shown and described in detail herein, including, for example, surgical instruments employing other translating cutting mechanisms, such as surgical staplers, and/or surgical instruments employing other translating or other mechanisms that can get stuck during motion from one position to another when performing a surgical procedure. Also, the disclosed methods and systems are not limited to detecting a fault condition of a cutting element, but could be implemented for a variety of surgical procedures by monitoring the time to perform an automatic operation and detecting the beginning of the operation and an end of the operation within the monitored time to detect a fault in the system.

Those having ordinary skill in the art would appreciate that the detection of the positions of the end effector component described above are not limited to using a limit switch to detect the positions and any of a variety of components, such as, for example, optical sensors, encoders, hall sensors, etc., may be used to detect the positions of the end effector component to perform the fault condition determination.

Exemplary embodiments, including the various operational methods described herein, can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure can be implemented by a processor 50 of or in conjunction with the electronics/control console 3000, and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

As described above, the methods and systems in accordance with various exemplary embodiments can be used in conjunction with a surgical instrument having an end effector configured to perform multiple surgical procedures via components that are actuated via a transmission mechanism at the proximal end of the instrument. In an exemplary embodiment, as described above, the end effector may be a combined fusing, gripping and cutting end effector as shown and described, for example, in U.S. patent application Ser. No. 13/399,391, entitled "FUSING AND CUTTING SURGICAL INSTRUMENT AND RELATED METHODS," filed on Feb. 17, 2012, which claims the benefit of priority to U.S. Provisional Patent Application No. 61/444,400, filed on Feb. 18, 2011 and to U.S. Provisional Patent Application No. 61/491,719, filed on May 31, 2011, the disclosures of which are incorporated herein by reference in their entireties.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are nonlimiting, and modifications to structure, dimensions, materials, and methodologies may be made without departing from the scope of the present teachings. For example, various aspects have been described in the context of an instrument used in a surgical robotic system. But these aspects may be incorporated into hand-held instruments as well.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgical system comprising:
  a surgical instrument comprising:
    a shaft having a proximal end portion and a distal end portion,
    an end effector coupled to the distal end portion of the shaft, the end effector comprising an end effector component and opposing jaw members having a length extending in a distal direction from the shaft, wherein the end effector component is configured to translate relative to the opposing jaw members and along a lengthwise direction of the opposing jaw members between a first position and a second position; and
  a controller in signal communication with the surgical instrument, wherein the controller is configured to:
    receive a first signal indicating that the end effector component is positioned between the first position and the second position,
    receive a second signal indicating that the end effector component is in one of the first position or the second position, and
    when the second signal is not received within a predetermined delayed response time period after the controller receives the first signal, transmit a control signal to automatically control operation of the end effector component.

2. The system according to claim 1, wherein the controller is configured to transmit the control signal to subject the end effector component to an oscillating driving force.

3. The system according to claim 2, wherein the oscillating driving force is higher in a first direction of oscillation than in a second direction of the oscillation.

4. The system according to claim 3, wherein the first direction is in a proximal direction of the surgical instrument and the second direction is in a distal direction of the surgical instrument.

5. The system according to claim 2, wherein the controller is configured to transmit the control signal to subject the end effector component to the oscillating force for a predetermined number of cycles.

6. The system according to claim 5, wherein the controller is configured to transmit a second control signal that subjects the end effector component to a directional driving force for moving the end effector component in a proximal direction of the surgical instrument after subjecting the end effector component to the oscillating force for the predetermined number of cycles.

7. The system according to claim 1, further comprising an output unit configured to output feedback indicating a fault condition of the end effector component when the second signal is not received within the predetermined delayed response time period after the controller receives the first signal.

8. The system according to claim 1, wherein the predetermined delayed response time period is at least a total period of time for the end effector component to move from the first position to the second position, and back to the first position.

9. The system according to claim 1, wherein the predetermined delayed response time period is at least a total period of time required for the end effector component to move from the first position to the second position.

10. The system according to claim 1, wherein the predetermined delayed response time period is at least a total period of time required for the end effector component to move from the second position to the first position.

11. The system according to claim 1, further comprising a sensor in signal communication with the controller, wherein the sensor is configured to output both the first signal and the second signal to the controller.

12. The system according to claim 1, wherein the end effector component comprises a cutting blade.

13. The system according to claim 1, wherein the controller is further configured to transmit a second control signal to open the opposing jaw members by a predetermined amount when the second signal is not received within the predetermined delayed response time period after the controller receives the first signal.

14. The system according to claim 1, further comprising a limit switch operable between two states based on a position of the end effector component, the limit switch being configured to generate the first signal and the second signal.

15. The system according to claim 1, further comprising a DC motor operably coupled to the end effector component, the control signal controlling voltage supplied to the DC motor.

16. The system of claim 7, wherein the output unit is configured to output at least one of visual and auditory feedback.

* * * * *